US012589240B2

(12) United States Patent
Muccio

(10) Patent No.: US 12,589,240 B2
(45) Date of Patent: Mar. 31, 2026

(54) MUSCLE STIMULATION SYSTEM

(71) Applicant: AxioBionics LLC, Ann Arbor, MI (US)

(72) Inventor: Philip Muccio, Ypsilanti, MI (US)

(73) Assignee: AxioBionics LLC, Ann Arbor, MI (US)

( * ) Notice: Subject to any disclaimer, the term of this patent is extended or adjusted under 35 U.S.C. 154(b) by 0 days.

(21) Appl. No.: 17/654,460

(22) Filed: Mar. 11, 2022

(65) Prior Publication Data

US 2023/0285743 A1　　Sep. 14, 2023

(51) Int. Cl.
| | |
|---|---|
| *A61N 1/00* | (2006.01) |
| *A61N 1/04* | (2006.01) |
| *A61N 1/08* | (2006.01) |
| *A61N 1/36* | (2006.01) |

(52) U.S. Cl.
CPC ......... *A61N 1/0452* (2013.01); *A61N 1/0484* (2013.01); *A61N 1/08* (2013.01); *A61N 1/36003* (2013.01); *A61N 1/36034* (2017.08); *A61N 2001/083* (2013.01)

(58) Field of Classification Search
CPC ...... A61N 1/0452; A61N 1/0484; A61N 1/08; A61N 1/36003; A61N 1/36034; A61N 2001/083
See application file for complete search history.

(56) References Cited

U.S. PATENT DOCUMENTS

| | | | |
|---|---|---|---|
| 1,548,711 | A | 8/1925 | Cooper |
| 4,252,112 | A | 2/1981 | Joyce |

| | | | | |
|---|---|---|---|---|
| 4,381,012 | A | 4/1983 | Russek | |
| 4,838,272 | A | 6/1989 | Lieber | |
| 6,428,495 | B1 | 8/2002 | Lynott | |
| 9,272,139 | B2 | 3/2016 | Hamilton et al. | |
| 10,092,762 | B2 | 10/2018 | Jiang et al. | |
| 2002/0058972 | A1 | 5/2002 | Minogue et al. | |
| 2003/0065369 | A1* | 4/2003 | Leyde ...................... | A61N 1/08 607/48 |
| 2004/0199095 | A1 | 10/2004 | Frangi | |
| 2005/0197599 | A1 | 9/2005 | Yu | |
| 2009/0105795 | A1* | 4/2009 | Minogue ................ | A61N 1/321 607/148 |
| 2010/0130847 | A1 | 5/2010 | Dunagan | |

(Continued)

FOREIGN PATENT DOCUMENTS

| | | |
|---|---|---|
| CA | 2906558 A1 | 9/2014 |
| CN | 106037731 A | 10/2016 |

(Continued)

OTHER PUBLICATIONS

"Bluetooth Basics" Sparkfun.*

(Continued)

*Primary Examiner* — Lynsey C Eiseman

(74) *Attorney, Agent, or Firm* — Mindful IP PLLC

(57) ABSTRACT

A muscle stimulation system includes an electrical stimulation garment and a stimulation controller. The stimulation controller has a stimulation processor programmed to identify the electrical stimulation garment and execute a treatment protocol associated with the electrical stimulation garment. A method includes determining a type of electrical stimulation garment and selecting a treatment protocol based at least in part on the type of electrical stimulation garment detected.

9 Claims, 8 Drawing Sheets

(56) References Cited

U.S. PATENT DOCUMENTS

| | | | |
|---|---|---|---|
| 2012/0016440 A1* | 1/2012 | Muccio ................ | A61N 1/0452 |
| | | | 607/48 |
| 2012/0065538 A1 | 3/2012 | Friedman | |
| 2012/0330394 A1 | 12/2012 | Dar et al. | |
| 2013/0158627 A1 | 6/2013 | Gozani et al. | |
| 2013/0238048 A1* | 9/2013 | Almendinger ....... | A61N 1/0509 |
| | | | 607/40 |
| 2014/0081353 A1* | 3/2014 | Cook ................... | A61N 1/3758 |
| | | | 607/59 |
| 2014/0257429 A1* | 9/2014 | Mohn ................ | A61N 1/36034 |
| | | | 607/48 |
| 2015/0119781 A1 | 4/2015 | Ponce | |
| 2017/0181703 A1* | 6/2017 | Kaib ................... | A61N 1/3943 |
| 2017/0368345 A1 | 12/2017 | Kong et al. | |
| 2018/0028808 A1* | 2/2018 | Ferree ................. | A61B 5/4815 |
| 2018/0125689 A1* | 5/2018 | Perez ................ | A61N 1/36014 |
| 2018/0289945 A1 | 10/2018 | Lampo | |
| 2019/0001133 A1* | 1/2019 | Onarheim ............ | A61N 1/0456 |
| 2020/0094043 A1* | 3/2020 | Dernebo ............. | A61N 1/0452 |
| 2020/0406035 A1* | 12/2020 | Sharma ..................... | A61F 2/72 |
| 2022/0016413 A1* | 1/2022 | John ................. | A61N 1/36034 |

FOREIGN PATENT DOCUMENTS

| | | | |
|---|---|---|---|
| WO | 2010027874 A2 | 3/2010 | |
| WO | 2020200498 A1 | 10/2020 | |

OTHER PUBLICATIONS

Shalaby, et al., Amplifier design for EMG recording from stimulation electrodes during functional electrical stimulation leg cycling ergometry, Published Dec. 17, 2010.

* cited by examiner

MUSCLE STIMULATION SYSTEM

BACKGROUND

Electrical stimulation (sometimes called "e-stim") is one way to improve physical therapy outcomes. It involves sending a mild electrical pulse through the skin to mimic the action of signals coming from neurons. These mild electrical currents target either muscles or nerves to help stimulate injured muscles or manipulate nerves to reduce pain. E-stim uses small electrodes placed on the skin with sticky pads that should come off with little discomfort at the end of a treatment session. Several electrodes are placed around the area receiving treatment. Wires from the electrical-stimulation device are attached to the pads. Steady streams of electrical pulses are delivered through the wires from the electrical-stimulation unit.

DETAILED DESCRIPTION

Figure 1:
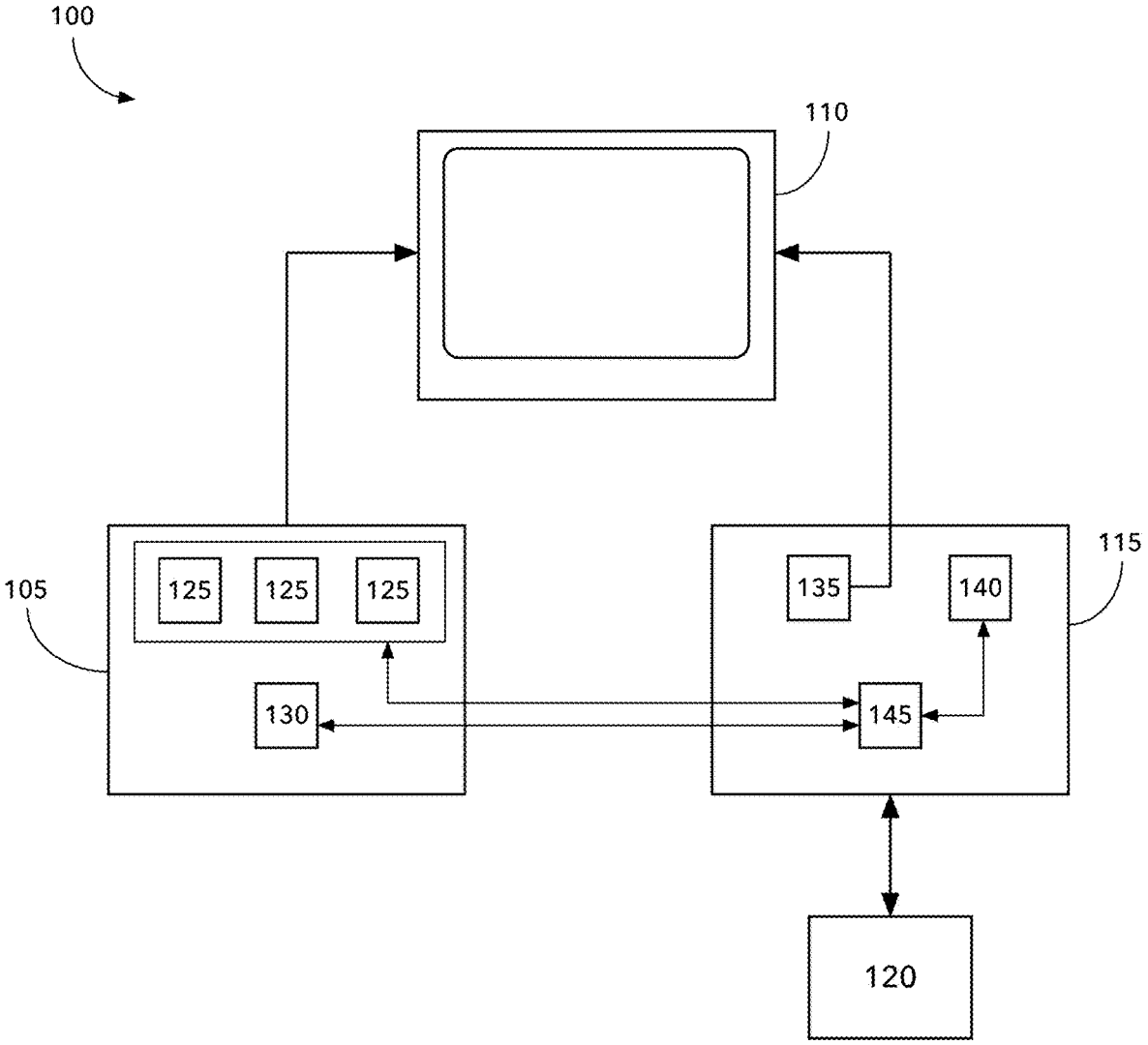
FIG. 1 illustrates an example block diagram showing example components of a muscle stimulation system including an example electrical stimulation garment.

Conventional electrical stimulation includes exposing the portion or the area of the body of the patient requiring the treatment in the form of electrical stimulation, applying a set of electrodes to the skin of the body of the patient, functional and structural coupling of the applied electrodes to an electrical stimulator, making incremental changes in the stimulation provided by the electrical stimulator being made until the patient feels comfort, and observing the patient during the treatment for muscle spasm or pain relief. To be effective, conventional electrical stimulation requires a physical therapist be present with the patient during the treatment, limiting treatment to times when the patient and physical therapist are both available.

Conventional at-home or over-the-counter muscle stimulation garments are not a replacement for physical therapy. Such stimulation garments apply generic treatment protocols that may or may not be effective for the patient. Moreover, without proper training on how to wear the garment, the patient may end up using the garment improperly. For instance, the patient may apply the garment to the wrong body part or otherwise wear the garment in a way that fails to provide the muscle stimulation required to provide a therapeutic benefit.

One solution is to provide a wearable electrode garment that can automatically stimulate the patient's muscles to provide the appropriate therapy. The wearable electrode garment can stimulate, e.g., one or more muscles and oftentimes four to ten muscles, simultaneously. During an initial setup, the physical therapist develops a treatment plan that is uploaded to the garment. The patient uses the garment as prescribed, and the garment automatically performs the treatment developed by the physical therapist. In some instances, the garment can detect whether it is placed on the appropriate body part and can limit its operation accordingly. That is, if placed on the wrong body part or in an incorrect orientation, the garment may limit the amount of stimulation or not provide any stimulation at all until the garment is worn correctly.

The concepts discussed herein can be applied to different types of electrical stimulation procedures for physical therapy. For instance, the concepts presented herein can be applied to Transcutaneous Electrical Neuromuscular Stimulation (TENS) for acute and chronic pain, Iontophoresis for calcific tendonitis, Neuromuscular Electrical Stimulation (NMES) for muscle contractions, Interferential Current (IFC) for improving localized blood flow in the body and High Voltage Galvanic Current (HVGC) for improving joint mobility, among others.

The muscle stimulation system disclosed herein includes an electrical stimulation garment and a stimulation controller. The stimulation controller has a stimulation processor programmed to identify the electrical stimulation garment and execute a treatment protocol associated with the electrical stimulation garment.

The electrical stimulation garment may include a garment processor programmed to output a unique code to the stimulation controller. The stimulation processor may be programmed to identify the electrical stimulation garment based at least in part on the unique code output by the garment processor. The stimulation processor may be programmed to select the treatment protocol based at least in part on the unique code output by the garment processor.

The unique code may identify a type of garment on which the garment processor is located. The electrical stimulation garment may include a plurality of electrodes. Executing the treatment protocol may include outputting signals to the plurality of electrodes. At least one of the stimulation processor and the garment processor may be programmed to measure an electrode impedance for each of the electrodes relative to a patient's skin. At least one of the stimulation processor and the garment processor may be programmed to determine that at least one electrode has failed based at least in part on the measured electrode impedance.

The plurality of electrodes may include a common electrode, a first electrode, and a second electrode, each connected to one another. At least one of the stimulation processor and the garment processor may be programmed to determine that at least one of the first electrode and the second electrode has failed based at least in part on a resistance between at least one of the common electrode and the first electrode, the common electrode and the second electrode, and the first electrode and the second electrode.

The treatment protocol may include a ramp-up phase, a stimulation phase, a ramp-down phase, and a post-stimulation phase. Each of the ramp-up phase, the stimulation phase, the ramp-down phase, and the post-stimulation phase occur over a period of time. The stimulation processor may be programmed to determine the period of time for each of the ramp-up phase, the stimulation phase, the ramp-down phase, and the post-stimulation phase based at least in part on the electrical stimulation garment identified.

The electrical stimulation garment may include a first wearable item and a second wearable item. In such instances, the stimulation processor may be programmed to identify the first wearable item and second wearable item and execute a treatment protocol associated with the first wearable item and the second wearable item.

A method includes determining a type of electrical stimulation garment and selecting a treatment protocol based at least in part on the type of electrical stimulation garment detected.

The method may further include monitoring an impedance of at least one electrode of the electrical stimulation garment. The method may further include determining an improper electrode connection based at least in part on the impedance of the at least one electrode. The method may further include providing a current flow to at least one electrode in accordance with the treatment protocol and stopping the current flow to the at least one electrode as a result of determining an improper electrode connection. The method may further include determining that a patient has taken a corrective action to resolve the improper electrode connection. The method may further include resuming the treatment protocol as a result of determining that the patient has taken the corrective action to resolve the improper electrode connection. Resuming the treatment protocol may include increasing an amount of electrical stimulation over a predetermined period of time after determining that the patient has taken the corrective action to resolve the improper electrode connection.

The elements shown may take many different forms and include multiple and/or alternate components and facilities. The example components illustrated are not intended to be limiting. Indeed, additional or alternative components and/or implementations may be used. Further, the elements shown are not necessarily drawn to scale unless explicitly stated as such.

As illustrated in FIG. 1, a stimulation system 100 includes an electrical stimulation garment 105, an interface device 110, a stimulation controller 115, and a power supply 120. Although the term "garment" is used, the stimulation system 100 may be incorporated into any type of apparel, accessory, or any other wearable item, regardless of whether the wearable item is traditionally thought of as a "garment."

The electrical stimulation garment 105 may be a wearable garment used for physical therapy such as a belt, arm sleeve, leg sleeve, wrap, cuff, etc. The wearable garment 105 may be formed from a clothing material such as cotton, neoprene, polyester, or any other material or blend of materials. In some instances, such as when the "garment" is another type of wearable item, such as a cuff, the garment 105 may be at least partially formed from, e.g., plastic or another material. The electrical stimulation garment 105 includes electronics such as electrodes 125 and a garment processor 130.

The electrodes 125 include metal wires, leads, or traces that extend from the garment processor 130 and through the garment 105 for contacting the patient's skin. In some instances, the electrodes 125 carry electricity, and the patient's skin may complete an electrical circuit between at least two electrodes 125. For instance, the electrodes 125 may include anode electrodes and cathode electrodes. The anode electrodes may receive control signals from the stimulation controller 115, and in response, transmit electrical current through the patient's body to the cathode electrodes. The cathode electrodes may receive the electrical current and complete the circuit back to the stimulator.

The garment processor 130 is implemented via circuits, chips, or other electronic components that energize the electrodes 125. For instance, the garment processor 130 may control the amount of electricity output by the electrodes 125. In some instances, the garment processor 130 may further receive and process signals representing the amount of electrical stimulation provided to the patient, how the patient's body responded to the electrical stimulation, the impedance of the patient, or the like. Moreover, the garment processor 130 may output a unique code that can be used to identify the garment 105 or the appropriate treatment protocol, as discussed in greater detail below.

The interface device 110 is implemented via circuits, chips, or other electronic components that can process signals and display information to, e.g., a user. The user may be the person seeking physical therapy treatment, the physical therapist, or someone else. The interface device 110 may receive signals output by the garment processor 130, the electrodes 125, or the stimulation controller 115, process the signals to develop treatment data, and display a visual representation of the treatment data to the user via, e.g., a display screen. For instance, the treatment information may identify the type of garment worn by the user, the treatment protocol implemented by the garment 105, the amount of impedance detected during treatment, or the like. In some instances, the display screen includes a touchscreen. In another possible implementation, the interface device 110 includes real or virtual buttons for receiving inputs from the user.

The stimulation controller 115 is implemented via circuits, chips, or other electronic components that control the operation of the garment 105, the interface device 110, or both. As shown in FIG. 1, the stimulation controller 115 includes a hardware interface 135, a memory 140, and a stimulation processor 145.

The hardware interface 135 is implemented via sensors, circuits, chips, or other electronic components that can electronically communicate with the garment processor 130, the electrodes 125, and the interface device 110. For instance, the hardware interface 135 may include electronic components configured to monitor operation of the electrodes 125, such as the signals output by the electrodes 125, and determine whether the electrodes 125 are operating properly, following a specified treatment protocol, or the like. The hardware interface 135 may further include a sensor configured to detect and/or identify the garment processor 130 based on, e.g., a unique code output by the garment processor 130. Examples of such sensors may include a communication chip configured to implement Bluetooth®, near-field communication (NFC), or another short-range communication protocol.

The memory 140 is implemented via circuits, chips or other electronic components and can include one or more of read only memory (ROM), random access memory (RAM), flash memory, electrically programmable memory (EPROM), electrically programmable and erasable memory (EEPROM), embedded MultiMediaCard (eMMC), a hard drive, or any volatile or non-volatile media etc. The memory 140 may store instructions executable by the stimulation processor 145 and data such as treatment protocols and/or historical data associated with the use of the garment 105.

The stimulation processor 145 is implemented via circuits, chips, or other electronic components that can execute instructions stored in the memory 140. For instance, the stimulation processor 145 may access the treatment protocols stored in the memory 140 and output control signals to the garment processor 130 via the hardware interface 135.

Upon receipt of the control signals, the garment processor 130 may output signals to the electrodes 125 that apply the treatment defined by the treatment protocol.

The power supply 120 is implemented via components that can store and/or output electrical energy to the components of the garment 105, the stimulator, or both. As shown in FIG. 1, the power supply 120 is electrically connected to the stimulator. Alternatively or in addition, one or more power supplies may be connected directly to the garment 105. The power supply 120 may include components for plugging into an electrical outlet. In that case, the power supply 120 may include a voltage converter for converting AC voltage from the outlet to DC voltage for use by the components shown in FIG. 1. In other possible approaches, the power supply 120 may include a battery configured to output DC voltage to the components of the garment 105, the stimulation controller 115, or both.

Figure 2:
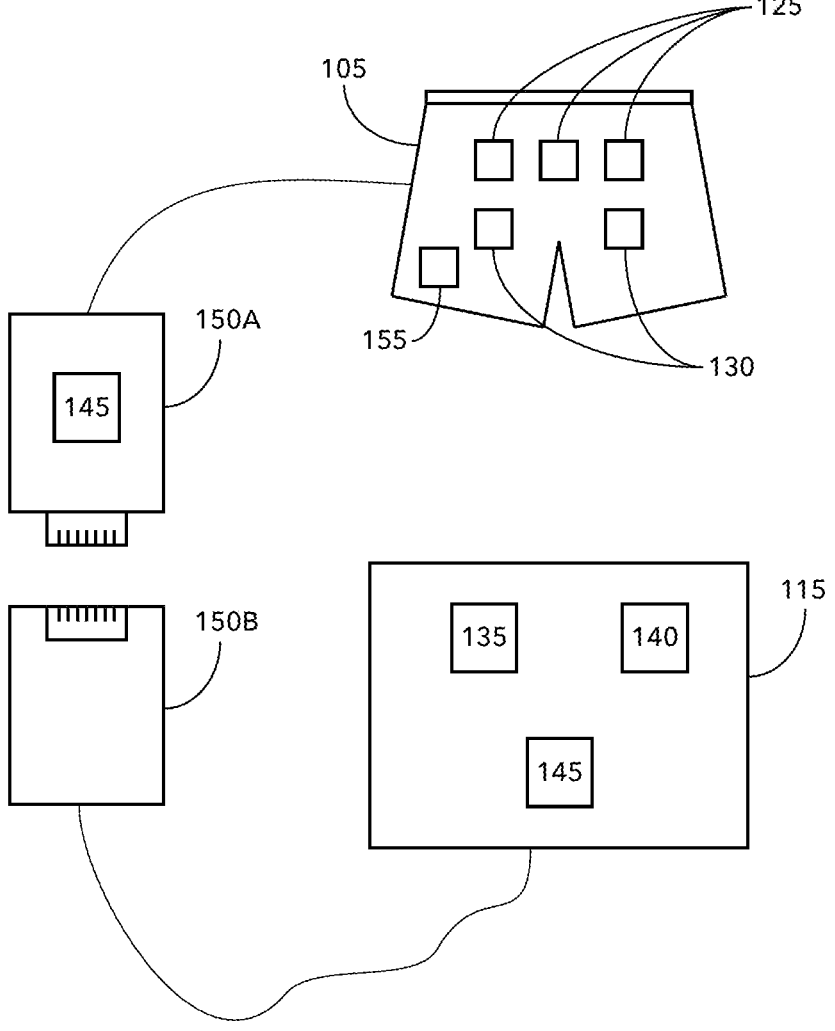
FIG. 2 is a schematic diagram showing example components of the muscle stimulation system.
Figure 3:
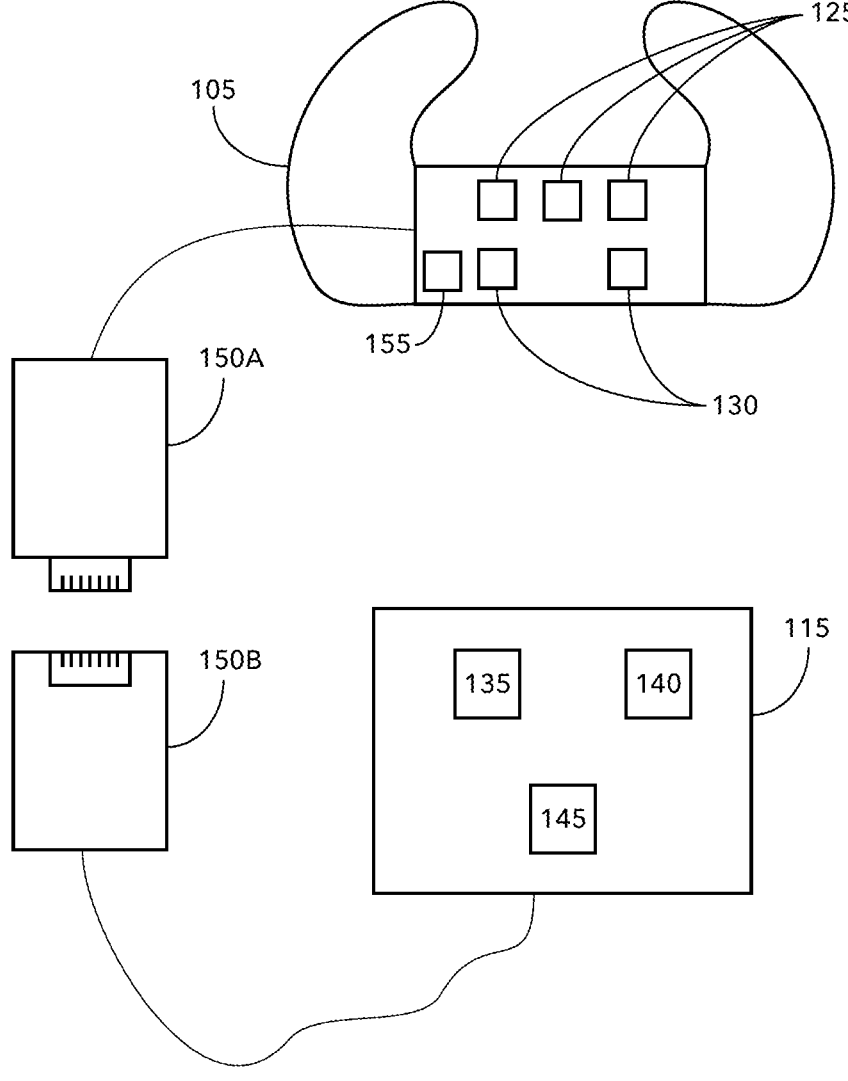
FIG. 3 is another schematic diagram showing example components of the muscle stimulation system.

FIGS. 2-3 are schematic diagrams showing example components of the garment 105, having the electrodes 125 and garment processor 130, taking the form of a pair of shorts (FIG. 2) and a wearable belt (FIG. 3). In the example of FIG. 2, the garment processor 130 is configured to output information indicating that the garment 105 is a pair of shorts. In the example of FIG. 3, the garment processor 130 is configured to output information indicating that the garment 105 is a wearable belt.

Also illustrated in both FIGS. 2 and 3 is a garment connector 150A implemented via electronic components configured to interface with the hardware interface 135 of the stimulation controller 115. For instance, the garment connector 150A may include a hardware interface 135, such as a universal serial bus (USB) interface, for plugging into the hardware interface 135, which may include corresponding hardware 150B for connecting to the garment connector 150A.

When the garment connector 150A is plugged into the hardware interface 135, the stimulation processor 145 may identify the type of wearable garment 105 based on the signals output by the garment processor 130. The stimulation processor 145 of FIG. 2 may determine that the garment 105 is a pair of shorts, select the appropriate treatment protocol from the memory 140 of the stimulation controller 115, and output the control signals associated with the selected treatment protocol. In this example approach, the selected treatment protocol and corresponding control signals are appropriate for stimulating certain muscles covered by shorts, such as the user's quads, hamstrings, and glutes. The stimulation processor 145 of FIG. 3 may determine that the garment 105 is a wearable belt, select the appropriate treatment protocol from the memory 140 of the stimulation controller 115, and output the control signals associated with the selected treatment protocol. In this example approach, the selected treatment protocol and corresponding control signals are appropriate for stimulating lower back muscles.

The garment 105 may further include an accelerometer 155 implemented via circuits, chips, or other electronic components that can detect a spatial orientation of the garment 105 and output signals representing the spatial orientation to the stimulation processor 145. The accelerometer 155, for example, may be programmed to output signals indicating that the patient is standing, lying down, sitting, walking, etc. The stimulation processor 145 may be programmed to delay or apply the appropriate treatment protocol in accordance with the patient's spatial orientation. For instance, if the treatment protocol requires the patient to be lying down, the stimulation processor 145 may delay the start of the treatment protocol if the patient is determined to be standing, sitting, walking, or in any other position other than lying down. If the patient stands up, the stimulation processor 145 may pause the treatment protocol until the patient resumes lying down.

In some instances, the treatment protocol is specific to the patient. Therefore, the garment processor 130 may communicate information about the patient and/or historical information about previous treatments, and the stimulation processor 145 may select the treatment protocol and output control signals based on the patient information, historical information, or both. By verifying the type of garment 105, patient information, and/or historical information, the garment processor 130 and stimulation processor 145 can reduce the likelihood of the wrong treatment protocol being applied to the patient.

Figure 4:
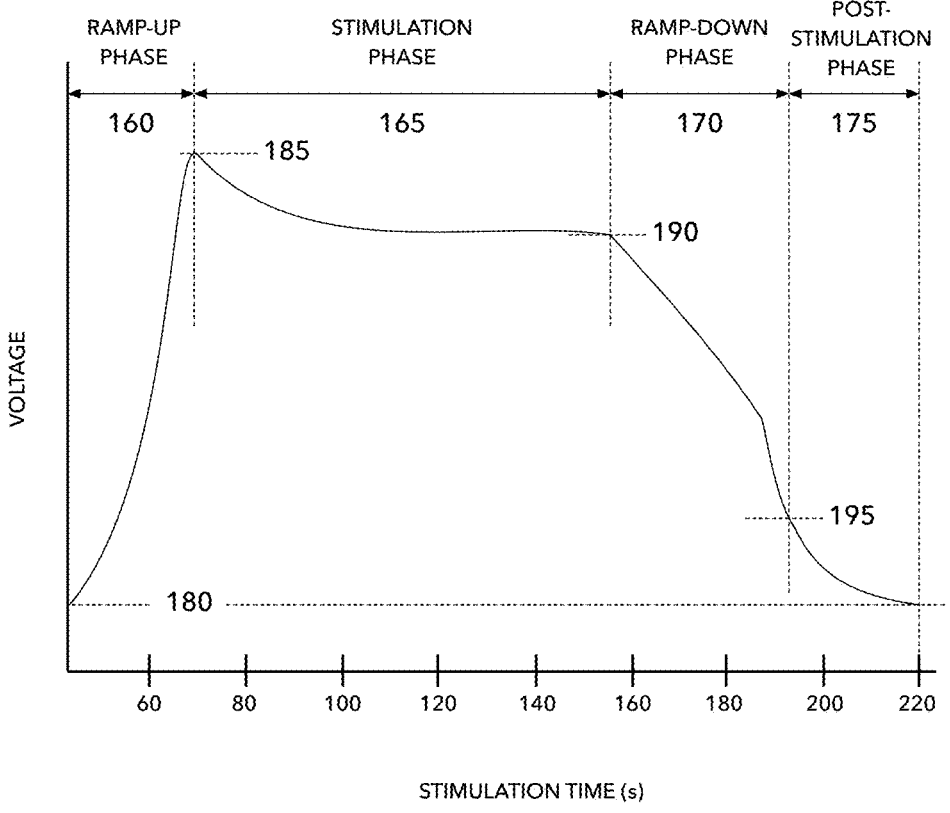
FIG. 4 is a graph showing a voltage variation over time.

FIG. 4 is a graph showing an example voltage variation over time for a particular treatment protocol. The treatment protocols can be tailored to the patient. Moreover, the start time of the treatment protocol can be delayed for a desired amount of time. For instance, the start time may be delayed by, e.g., 15-90 minutes to give the patient time to fall asleep before beginning the treatment.

The treatment protocol generally includes four phases: a ramp-up phase 160, a stimulation phase 165, a ramp-down phase 170, and a post-stimulation phase 175. During the ramp-up phase 160, the voltage increases quickly. In the example of FIG. 4, the voltage increases from an initial voltage 180 to a peak voltage 185 over a ramp-up time period, in this case, approximately 0-90 seconds, and typically 20-40 seconds.

During the stimulation phase 165, the voltage may change slightly. For instance, as shown in FIG. 4, the voltage drops from the peak voltage 185 to a first intermediate voltage 190 over a longer period of time than the ramp-up time period. For instance, the voltage may drop from the peak voltage 185 to the first intermediate voltage 190 over a period of, e.g., 40-80 seconds. Further, as shown in FIG. 4, the drop from the peak voltage 185 to the first intermediate voltage 190 may not be uniform, meaning the rate of change of the voltage drop be different throughout the stimulation period. That is, the rate of change may be faster at the beginning of the stimulation period and lower over time.

During the ramp-down phase 170, the voltage may drop from the first intermediate voltage 190 to a second intermediate voltage 195, lower than the first intermediate voltage 190. As shown in FIG. 4, the change in voltage during the ramp-down phase 170 occurs faster than the change in voltage during the stimulation phase 165 but slower than the change in voltage during the ramp-up phase 160. For instance, the ramp-down phase 170 may occur over a period of, e.g., 40-80 seconds. Moreover, the drop from the first intermediate voltage 190 to the second intermediate voltage 195 may not be uniform, meaning the rate of change of the voltage drop may be different throughout the ramp-down period. That is, the rate of change may be slower at the beginning of the ramp-down period and faster during, e.g., the last 10-20 seconds of the ramp-down period.

During the post-stimulation phase 175, the voltage may drop from the second intermediate voltage 195 to the initial voltage 180. As shown in FIG. 4, the change in voltage during the post-stimulation phase 175 occurs faster than the change in voltage during the stimulation phase 165 and ramp-down phase 170, and possibly faster than during the ramp-up phase 160. For instance, the ramp-down phase 170 may occur over a period of, e.g., 5-40 seconds. Moreover, the drop from the second intermediate voltage 195 to the initial voltage 180 may not be uniform, meaning the rate of change of the voltage drop may be different throughout the post-stimulation period. That is, the rate of change may be faster at the beginning of the post-stimulation period and slower during, e.g., the last 10-20 seconds of the ramp-down period.

The treatment protocol may repeat any number of times appropriate for the patient. In some instances, the treatment protocol may automatically start again after a desired amount of time, on the order of seconds, minutes, or hours. The treatment protocol may repeat over a period of time such as, e.g., 8 hours or another length of time appropriate for the treatment.

For situations where a custom treatment protocol is desired, a clinician may, using a mobile device, tablet computer, laptop computer, desktop computer, or the like, may present an interactive graphical user interface. For instance, the graphical user interface may include real or virtual sliders or buttons that allow the clinician to change the length and/or intensity of each phase of the treatment protocol. Moreover, the graphical user interface may allow the clinician to define a custom wave pattern for the electrical stimulation applied to the patient. That is, the graphical user interface may permit the clinician to manually adjust the duration and intensity of electrical impulses and define a treatment protocol appropriate for the patient's condition and comfort.

In some instances, the stimulation processor 145, the garment processor 130, or both, are configured to detect whether the electrodes 125 are attached to the patient's skin based on, e.g., a detected amount of impedance. If the impedance increases to, e.g., a peak impedance limit, suggesting an open circuit, the stimulation processor 145 or garment processor 130 may be programmed to determine that one or more electrodes 125 has become disconnected, at which point the stimulation processor 145 and/or garment processor 130 may be programmed to discontinue all voltage to the electrodes 125. In this example approach, the peak impedance limit may be a multiple of an expected impedance value of a person with, e.g., an electrode 125 gel applied between the electrode 125 and the person's skin.

Figure 5A:
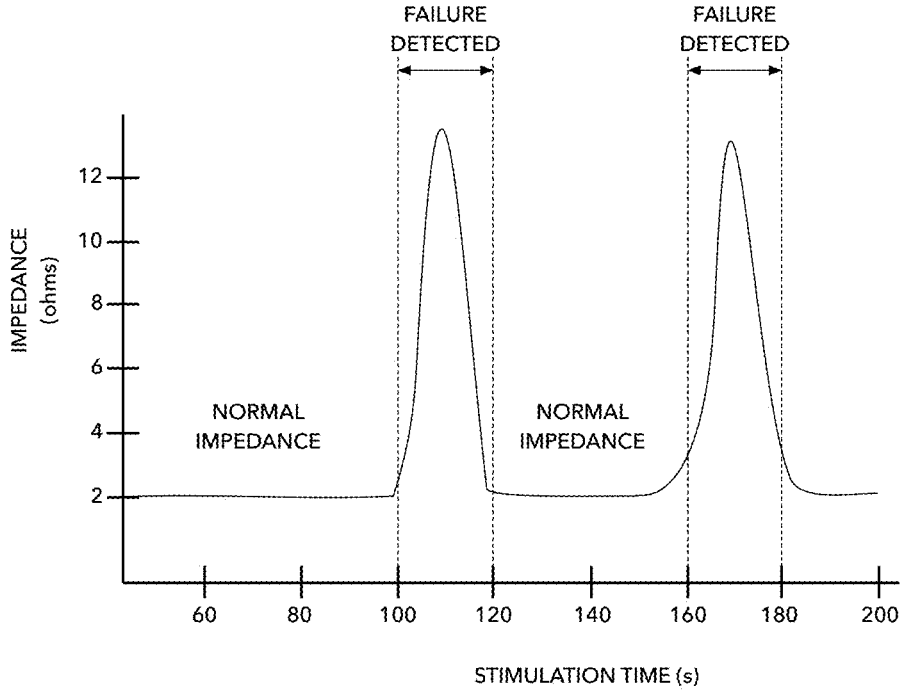
FIG. 5A is a graph showing how impedance can be used to detect a faulty electrode.
Figure 5B:
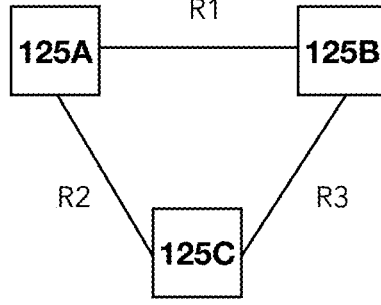
FIG. 5B is a schematic diagram showing an example circuit for detecting a faulty electrode.

FIG. 5A is a graph showing example impedance monitoring of the electrodes 125 over time. FIG. 5B is a schematic diagram showing one way to detect a faulty electrode 125. The electrodes 125 may move relative to the patient's skin over time as, for instance, the patient moves. The patient's movement may, in some instances, cause a gap between the electrode 125 and the patient's skin. As discussed in greater detail below, the stimulation processor 145 may be programmed to recognize such events and stop the stimulation from one or more electrodes 125. Moreover, the stimulation processor 145 may slowly resume stimulation to one or more of the electrodes 125 over a predetermined period of time on the order of, e.g., 5 to 90 seconds upon detecting that the impedance value has returned to normal. The stimulation may automatically resume, i.e., without any patient interaction. As such, the patient can wear the garment 105 comfortably throughout the day or night, even when sleeping, while minimizing the risk of discomfort or startling the patient when the stimulation resumes.

The stimulation processor 145 may be configured to output a constant direct current (DC) voltage signal to the electrodes 125 and calculate the impedance of each electrode 125. If the impedance exceeds the peak impedance limit, the stimulation processor 145 may determine that one or more electrodes 125 have become disconnected from the patient or have otherwise failed to make full contact with the skin. In that case, the stimulation processor 145 may cease to output control signals to the garment processor 130. In some instances, the stimulation processor 145 may be programmed to prompt the user, via the interface device 110, to review the placement of the electrodes 125, including whether a sufficient amount of gel has been placed between the user's skin and the electrode 125.

With reference to FIGS. 5A and 5B, the stimulation processor 145 may also be configured to distinguish between the anode electrodes and cathode electrodes for purposes of detecting connection issues. For instance, current flow between a common electrode 125A and one or both of the cathode electrode 125B and anode electrode 125C may be interrupted when there is a fault associated with one or both electrodes 125B, 125C. That is, if the current flow between the common electrode 125A and the cathode electrode 125B is lower than expected, or a high resistance R1 between the common electrode 125A and the cathode electrode 125B is detected, the stimulation processor 145 may determine that the cathode electrode 125B has separated from the patient's skin. Another indicator of separation of the cathode electrode 125B may be a high resistance R1 detected between the common electrode 125A and the cathode electrode 125B and also a high resistance R2 detected between the cathode electrode 125B and the anode electrode 125C. Likewise, if the current flow between the common electrode 125A and the anode electrode 125C is lower than expected, or a high resistance R3 between the common electrode 125A and the anode electrode 125C is detected, the stimulation processor 145 may determine that the anode electrode 125C has separated from the patient's skin. Another indicator of separation of the anode electrode 125C may be a high resistance R2 detected between the common electrode 125A and the anode electrode 125C and a high resistance R3 detected between the cathode electrode 125B and the anode electrode 125C. For instance, the common electrode 125A may be arranged in series with the cathode electrode 12B and anode electrode 125C and the stimulation processor may be programmed to measure the resistance R1, R2, R3 between the electrodes 125. From the resistance R1, R2, R3 measured, the stimulation processor 145 may be configured to determine which electrode 125— cathode 125B or anode 125C—has failed based at least in part on the impedance profile.

In another possible implementation, the garment processor 130 may output the DC voltage signal, detect the impedance values of the electrodes 125 relative to the patient's skin, and diagnose a failure of one or more electrodes 125. If the garment processor 130 detects an impedance that is higher than expected, the garment processor 130 may disable the electrodes 125 and/or communicate the failure to the stimulation processor 145. Moreover, the garment processor 130 may prompt the user, via the interface device 110, to confirm the placement of the electrodes 125 and/or that a sufficient amount of gel has been placed between the electrodes 125 and the user's skin.

Figure 6:
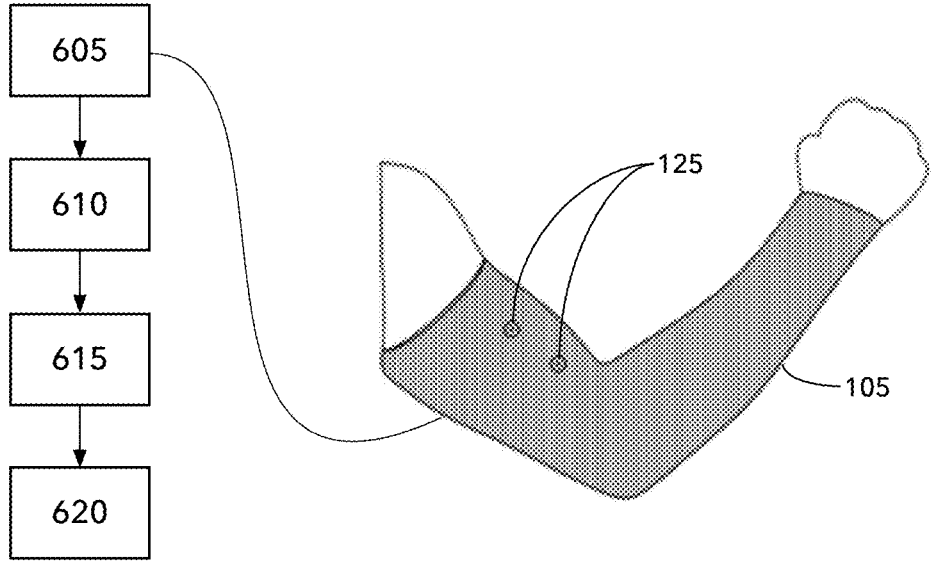
FIG. 6 is a schematic diagram of an implementation of the garment including an example arm sleeve.
Figure 7:
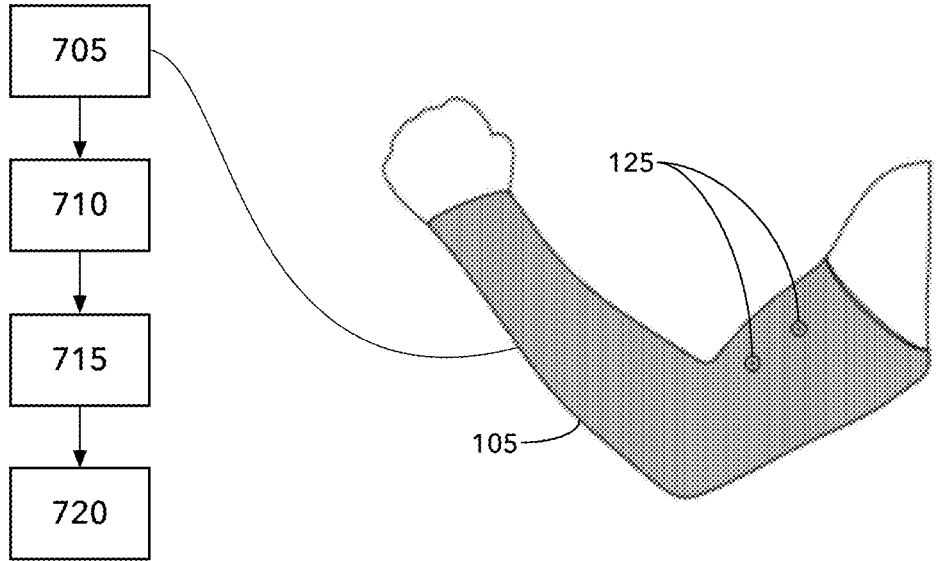
FIG. 7 is a schematic diagram of an implementation of the garment including another example arm sleeve.

FIGS. 6-7 are schematic diagrams of an implementation of the garment 105 including example arm sleeves to be worn by a patient. The garment 105 shown in FIG. 6 is meant to be worn on a patient's right arm and the garment 105 in FIG. 7 is meant to be worn on a patient's left arm. Both implementations involve electrically and/or communicatively coupling the stimulation controller 115 to the garment 105. As discussed previously, the stimulation controller 115 communicates with the garment processor 130 to detect the type of garment 105 worn by the patient (block 605/705). After verifying the type of garment 105, the garment stimulator confirms the connectivity with the garment process (block 610/710) and connectivity of the electrodes 125 using the techniques described previously to determine that the electrodes 125 are likely adhered to the patient's skin (block 615/715). Moreover, the garment stimulator monitors the voltage and time parameters to monitor the progress of the stimulation protocol and, e.g., notify the patient when the treatment for the particular body part(s) covered by the garment 105 is complete (block 620/720).

Figure 8:
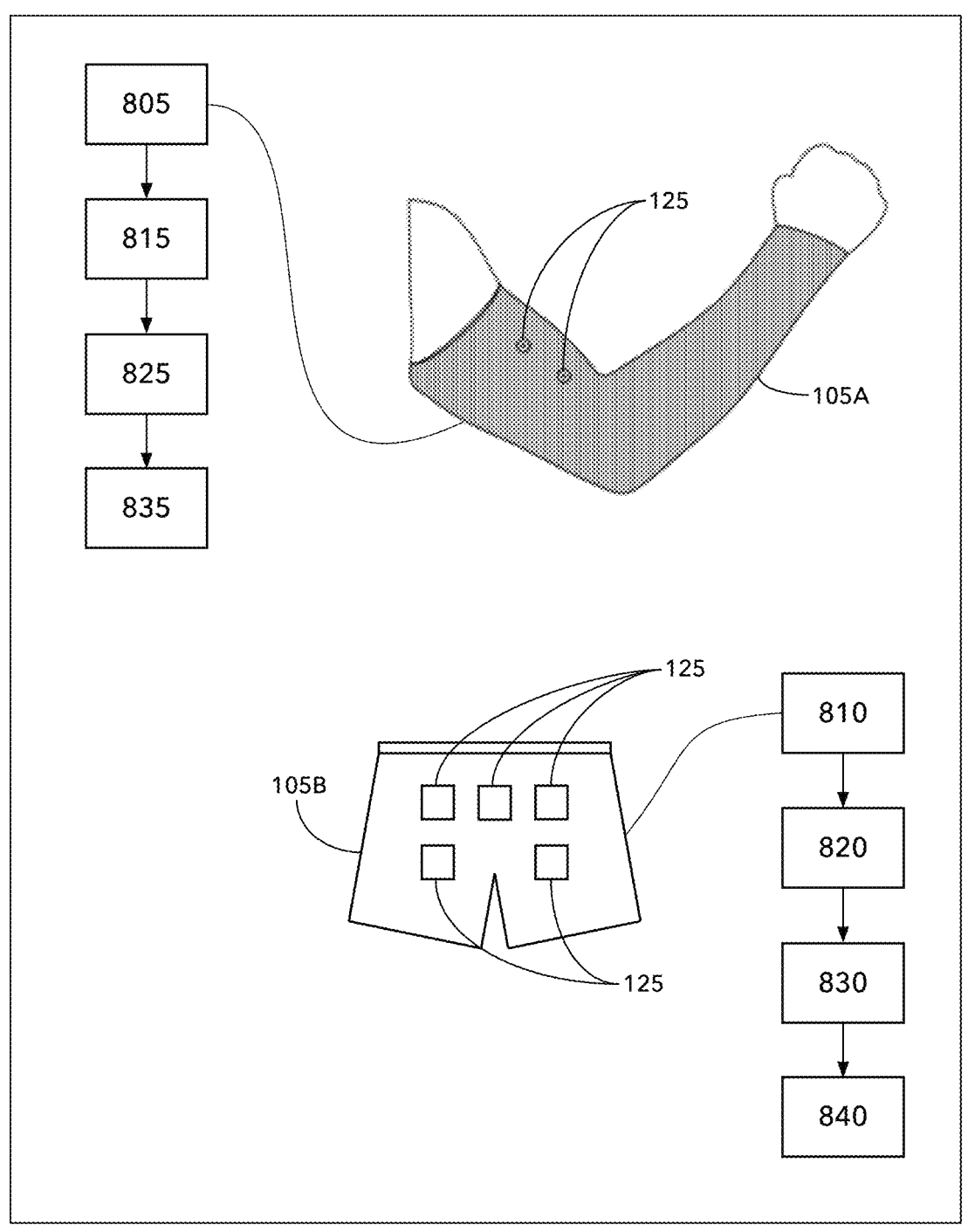
FIG. 8 is a schematic diagram showing an example implementation involving multiple garments worn simultaneously.

FIG. 8 is a schematic diagram showing an example implementation involving multiple garments 105A and 105B worn simultaneously. In the example shown in FIG. 8, the patient is wearing a left-arm sleeve 105A and a pair of shorts 105B for purposes of electrical stimulation of the patient's left arm and certain lower extremity muscles, respectively. In this example implementation, the stimulation controller 115 is electrically and/or communicatively coupled to the garments 105A and 105B, particularly to the garment processor 130 and/or electrodes 125 of each garment 105. As discussed previously, the stimulation controller 115 communicates with the garment processor 130 to detect the types of garments 105A and 105B worn by the patient (block 805/810). After verifying the types of garment 105, the garment stimulator confirms the connectivity with the garment processor 130 (block 815/820) and connectivity of the electrodes 125 using the techniques described previously to determine that the electrodes 125 of both garments 105A and 105B are likely adhered to the patient's skin (block 825/830). Moreover, the garment stimulator monitors the voltage and time parameters to monitor the progress of the stimulation protocol and, e.g., notify the patient when the treatment for the particular body part(s) covered by the garments 105A and 105B is complete (block 835/840). In this example approach, the stimulation controller 115 can simultaneously execute two treatment protocols for different body parts or muscle groups with reduced risk that the treatment protocol is applied to the wrong body part since the type of garment and placement of the garment on the patient's body is confirmed by the stimulation controller 115 before the treatment protocol begins.

Figure 9:
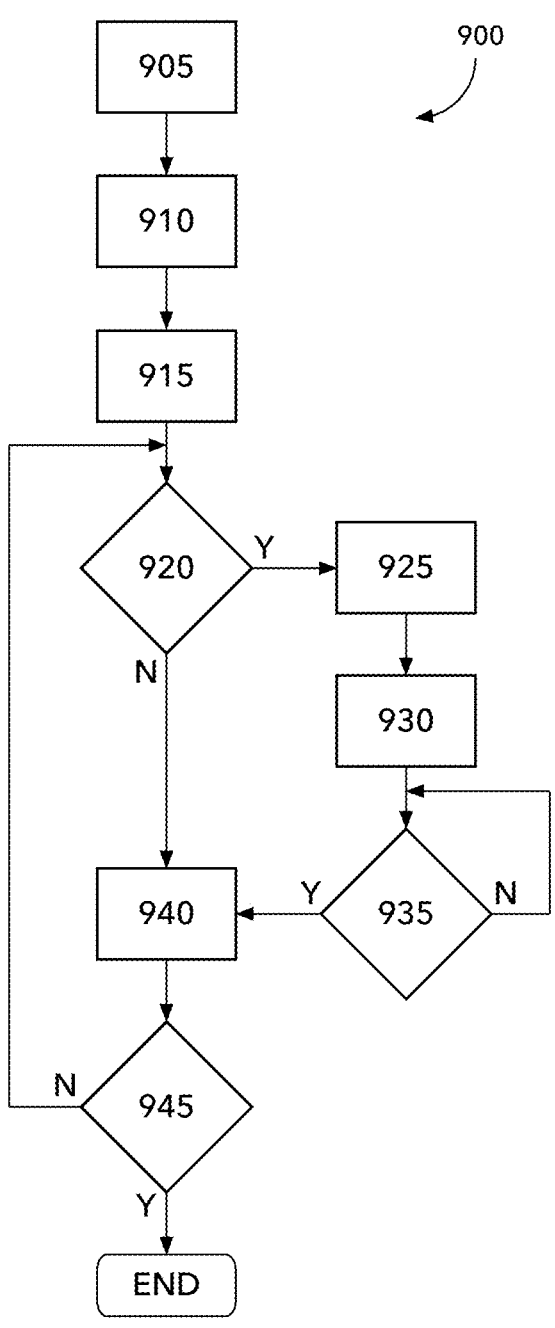
FIG. 9 is a flowchart of an example process that may be executed by the garment.

FIG. 9 is a flowchart of an example process 900 that may be executed by the stimulation controller 115. The process 900 may begin prior to starting a treatment protocol and may continue to execute until the treatment protocol is complete or the process 900 is otherwise stopped, as discussed below.

At block 905, the stimulation controller 115 determines the type of garment 105 worn by the patient. Determining the type of garment 105 may include the stimulation processor 145 communicating with the garment processor 130. For instance, the garment processor 130 may transmit, to the stimulation processor 145, information representing the type of garment 105. The stimulation processor 145 may determine the type of garment 105 worn by the patient based on such information provided by the garment processor 130. In some instances, such as the implementation shown in FIG. 8, multiple garments 105 may be identified as being worn by the patient simultaneously. For example, the stimulation controller 115 may determine that the patient is wearing both a first wearable item 105A and a second wearable item 105B and apply a treatment protocol associated with the first wearable item 105A and the second wearable item 105B.

At block 910, the stimulation controller 115 customizes stimulation treatment parameters associated with the operation of the electrodes 125 embedded in the garment 105 identified at block 905. For instance, the stimulation processor 145 may select the treatment parameters from among values stored in the memory 140 of the stimulation controller 115. In some instances, the stimulation processor 145 selects from among one or more parameters associated with the particular garment 105 identified at block 905. Parameters may include an on/off setting, pulse width, frequency, current intensity, time, ramp-up settings, ramp-down settings, and stimulation pulse.

At block 915, the stimulation controller 115 selects a stimulation treatment protocol. For instance, the stimulation processor 145 may select from among the treatment protocols stored in the memory 140 of the stimulation controller 115. The protocols may include a pain management protocol, a lower extremity eccentric protocol, a lower abdominal protocol, an abdominal protocol, a vertebrae vest protocol, and an upper extremity protocol. The stimulation processor 145 may select the protocol based, at least in part, on the type of garment 105 identified at block 905, the parameters set at block 910, or both.

At decision block 920, the stimulation controller 115 determines whether one or more of the electrodes 125 are faulty. Determining whether an electrode 125 is faulty may include monitoring the impedance of the electrode 125 relative to the patient's skin. A high impedance suggests that the electrode 125 has become disconnected from the patient or an insufficient amount of, e.g., gel was used to attach the electrode 125 to the patient. Additionally or in the alternative, the stimulation controller 115 may be programmed to evaluate the current flow through a common electrode 125A and another electrode 125B, 125C in series with the common electrode 125A. If the current flow drops to, e.g., approximately zero, the stimulation controller 115 may determine that the electrode 125B, 125C in series with the common electrode 125A has failed. Alternatively or in addition, the stimulation controller 115 may be programmed to measure a resistance R1 between the common electrode 125A and the cathode electrode 125B, a resistance R2 between the common electrode 125A and the anode electrode 125C, and a resistance R3 between the cathode electrode 125B and the anode electrode 125B. If high impedance or resistance R1, R2, R3, low current, or another indicator of a faulty electrode 125 is detected, the process 900 proceeds to block 925. Otherwise, the process 900 proceeds to block 940.

At block 925, the stimulation controller 115 disables the current flow to all electrodes 125 or to the faulty electrode if the electrode that is faulty can be detected. Disabling the current flow may include the stimulation processor 145 transmitting a signal to the garment processor 130 to turn off one or more electrodes 125. In some instances, disabling the current flow may include the stimulation processor 145 disconnecting one or more electrodes 125 from the power supply 120.

At block 930, the stimulation controller 115 prompts the patient to correct the issue. For instance, the stimulation processor 145 may output a signal to the interface device 110, causing the interface device 110 to present a message to the patient. The message may help the patient diagnose and correct the issue with the faulty electrode 125. For instance, if the faulty electrode 125 is the result of a lack of gel, the interface device 110 may instruct the patient to apply more gel to the electrode 125 before reattaching the electrode 125 to the patient's skin.

At decision block 935, the stimulation controller 115 determines whether the patient has taken the corrective action presented at block 930. The stimulation processor 145 may determine whether the patient has taken the corrective action by continuing to monitor, e.g., the impedance of the electrode 125. When the impedance drops to a level that indicates it is properly adhered to the patient, the stimulation processor 145 may determine that the patient has taken the corrective action, at which point, the process 900 may proceed to block 940. Otherwise, block 935 may be repeated until the corrective action is taken.

At block 940, the stimulation controller 115 ramps up the current flow to one or more electrodes 125. That is, the stimulation processor 145 may increase the current flow to the faulty electrode 125 and/or any other electrodes 125 disabled at block 925 over a predetermined period of time. The predetermined period of time may be on the order of several seconds to one or more minutes. For instance, the predetermined period of time may be 10-80 seconds. The process 900 may return to block 920 so the operation of the electrodes 125 can be reevaluated.

At decision block 945, the stimulation controller 115 determines whether the treatment protocol is complete. If so, the process 900 ends. Otherwise, the process 900 returns to block 920 so the electrodes 125 can be continually monitored.

Other features and functionality may be included in the process 900 or other processes executed by the stimulation controller 115. For instance, the stimulation controller 115 may communicate with a software application used by the patient, a clinician, or both, via a mobile device, tablet computer, laptop computer, desktop computer, or the like. The software application may measure and monitor various characteristics such as the amount of time the patient spent lying down, sitting, standing, walking, etc., during the treatment. The software application may further measure or monitor other information such as the patient's walking speed, number of steps per minute, etc. In some instances, the software application may track the length and quality of the patient's sleep as well as medication intake.

The software application may further collect and display information relating to electromyography (EMG) techniques representing nerve stimulation of certain muscles, electrocardiogram (ECG) processes used to evaluate the patient's heart conditions, pain associated with cutaneous electrical stimulation, or the like. In some example implementations, this information can be captured before treatment to establish baseline characteristics and compared to comparable information captured after treatment to show, objectively, whether treatment is working as expected. In some instances, the software application may receive information about the treatment protocol applied, and may further be used to present reminders or notifications to the patient when it is time for the next treatment.

The software application may cause the user's computing device to transmit information to a cloud-based server. The clinician may use a computing device, such as a mobile device, tablet computer, laptop computer, or desktop computer, to review the information captured by the software application running on the patient's computing device and modify the treatment protocol as needed. The software application on the patient's computing device may transmit signals representing the updated treatment protocol to the stimulation controller so the most up-to-date treatment protocol can be applied during the patient's next treatment.

In general, the computing systems and/or devices described may employ any of a number of computer operating systems, including, but by no means limited to, versions and/or varieties of the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the OS X, macOS, and iOS operating systems distributed by Apple Inc. of Cupertino, California, the BlackBerry OS operating system distributed by Blackberry, Ltd. of Waterloo, Canada, and the Android operating system developed by Google, Inc. and the Open Handset Alliance. Examples of computing devices include, without limitation, a computer workstation, a server, a desktop, notebook, laptop, or handheld computer, or some other computing system and/or device.

Computing devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc. Some of these applications may be compiled and executed on a virtual machine, such as the Java Virtual Machine, the Dalvik virtual machine, or the like. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their ordinary meanings as understood by those knowledgeable in the technologies described herein unless an explicit indication to the contrary is made herein. In particular, use of the singular articles such as "a," "the," "said," etc. should be read to recite one or more of the indicated elements unless a claim recites an explicit limitation to the contrary.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

The invention claimed is:

1. A muscle stimulation system comprising:
an electrical stimulation garment having a plurality of electrodes, an accelerometer, and a garment processor programmed to output a unique code to a stimulation controller identifying a type of the electrical stimulation garment; and
a stimulation controller including a stimulation processor programmed to:
upon receiving the unique code from the electrical stimulation garment, identify the type of the electrical stimulation garment based on the received unique code;
identify a spatial orientation of the electrical stimulation garment;

select a treatment protocol based on the type of the electrical stimulation garment from a set of treatment protocols stored in a memory of the stimulation controller;
and execute the selected treatment protocol that is associated with the type of the electrical stimulation garment by activating the plurality of electrodes;
and
wherein the electrical stimulation garment includes the plurality of electrodes and wherein executing the treatment protocol includes outputting signals to the plurality of electrodes, wherein the selected treatment protocol corresponds to stimulating specific muscles covered by the identified garment type; and wherein at least one of the stimulation processor and the garment processor is programmed to measure an electrode impedance for each of the plurality of electrodes relative to a patient's skin.

2. The muscle stimulation system of claim 1, wherein at least one of the stimulation processor and the garment processor is programmed to determine that at least one electrode has failed based at least in part on the measured electrode impedance.

3. The muscle stimulation system of claim 1, wherein the plurality of electrodes includes a common electrode, a first electrode, and a second electrode, each connected to one another, and wherein at least one of the stimulation processor and the garment processor is programmed to determine that at least one of the first electrode and the second electrode has failed based at least in part on a resistance between at least one of the common electrode and the first electrode, the common electrode and the second electrode, and the first electrode and the second electrode.

4. The muscle stimulation system of claim 1, wherein the treatment protocol includes a ramp-up phase, a stimulation phase, a ramp-down phase, and a post-stimulation phase.

5. The muscle stimulation system of claim 4, wherein each of the ramp-up phase, the stimulation phase, the ramp-down phase, and the post-stimulation phase occur over a period of time.

6. The muscle stimulation system of claim 5, wherein the stimulation processor is programmed to determine the period of time for each of the ramp-up phase, the stimulation phase, the ramp-down phase, and the post-stimulation phase based at least in part on the electrical stimulation garment identified.

7. A method comprising:
determining a type of an electrical stimulation garment;
selecting a treatment protocol from a memory of a stimulation controller that is separate from the electrical stimulation garment, the treatment protocol based at least in part on the type of the electrical stimulation garment detected and a spatial orientation of the electrical stimulation garment;
providing a current flow to at least one electrode supported by the electrical stimulation garment in accordance with the treatment protocol;
executing the treatment protocol further includes outputting signals to the at least one electrode, and
measuring an electrode impedance for each of the at least one electrode relative to a patient's skin,
wherein a garment processor included in the electrical stimulation garment is programmed to output a unique code to the stimulation controller wherein the unique code identifies the type of the electrical stimulation garment; and wherein the stimulation controller selects the treatment protocol based on the type of the electrical stimulation garment from a set of treatment protocols programmed into the memory of the stimulation controller;

stopping the current flow to the at least one electrode as a result of determining an improper electrode connection; and automatically resuming the treatment protocol, without a patient interaction, as a result of determining that an impedance value has returned to normal, wherein resuming the treatment protocol includes increasing an amount of electrical stimulation over a predetermined period of time after determining that the impedance value has returned to normal.

8. The method of claim 7, further comprising monitoring the electrode impedance of the at least one electrode of the electrical stimulation garment.

9. The method of claim 8, further comprising determining an improper electrode connection based at least in part on the electrode impedance of the at least one electrode.

* * * * *